(12) United States Patent
Budd et al.

(10) Patent No.: US 7,998,990 B2
(45) Date of Patent: Aug. 16, 2011

(54) 5-PHENYL-THIAZOL-2-YL-UREA DERIVATIVES AND USE AS PI3 KINASE INHIBITORS

(75) Inventors: Emma Budd, Horsham (GB); Judy Fox Hayler, Horsham (GB); Ian Bruce, Horsham (GB); Darren Mark Legrand, Horsham (GB); Brian Cox, Horsham (GB)

(73) Assignee: Novartis AG, Basel (CH)

( * ) Notice: Subject to any disclaimer, the term of this patent is extended or adjusted under 35 U.S.C. 154(b) by 103 days.

(21) Appl. No.: 12/227,315

(22) PCT Filed: May 21, 2007

(86) PCT No.: PCT/EP2007/004500
§ 371 (c)(1),
(2), (4) Date: Nov. 12, 2008

(87) PCT Pub. No.: WO2007/134827
PCT Pub. Date: Nov. 29, 2007

(65) Prior Publication Data
US 2009/0234132 A1 Sep. 17, 2009

(30) Foreign Application Priority Data
May 23, 2006 (GB) .................................. 0610243.8

(51) Int. Cl.
*A61K 31/426* (2006.01)
*C07D 277/42* (2006.01)
(52) U.S. Cl. ....................................... 514/371; 548/196
(58) Field of Classification Search .................. 548/196; 514/371
See application file for complete search history.

(56) References Cited

FOREIGN PATENT DOCUMENTS
| | | |
|---|---|---|
| WO | WO 03/072557 | 9/2003 |
| WO | WO 2005/021519 | 3/2005 |
| WO | WO 2007/068473 | 6/2007 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Vippagunta, et al. Advanced Drug Delivery Reviews 48 (2001) 3-26.*
Rheumatoid arthritis [online] retrieved on Aug. 14, 2010. (URL:http://www. medicinenet.com/rheu matoid_arth ritis/article, htm>).*
Diabetes [online] retrieved on Apr. 15, 2009 from the internet [http:llwww.merck.com/mmpe/print/sec121ch1581ch158b.html].*
Asthma [online] retrieved on Oct. 23, 2010 from the internet (URL; https://health.google.com/health/ref/Asthma.*
Chronic obstructive pulmonary disease [online] retrieved on Oct. 23, 2010 from the internet (URL; http://www.nlm.nih.gov/medlineplus/ency/article/000091.htm).*

* cited by examiner

*Primary Examiner* — Shawquia Young
(74) *Attorney, Agent, or Firm* — Paul D. Strain; Strain & Strain PLLC

(57) ABSTRACT

The present invention concerns a compound of formula Ia wherein: $R^{a*}$ is hydrogen or $C_1$-$C_4$-alkyl; $R^{b*}$ is —($C_1$-$C_4$-alkylene)-Y—$C_1$-$C_4$-haloalkyl or —($C_1$-$C_4$-alkylene)-Y—$C_1$-$C_4$-hydroxyalkyl; Y represents —CONH— or a five membered heteroaryl group. $R^{2*}$ is $C_1$-$C_4$-alkyl or halogen; $R^{3*}$ is halo, —$SO_2$—$CH_3$, —$SO_2$—$CF_3$, carboxy, —CO—$NH_2$, —CO-di($C_1$-$C_8$-alkyl)amino, or a 5- or 6-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino; $R^{4*}$ is hydrogen, halo, —$SO_2$—$CH_3$, nitrile, $C_1$-$C_8$-haloalkyl, imidazolyl, $C_1$-$C_8$-alkyl, —$NR^{8*}R^{9*}$, or —$SO_2$—$NR^{8*}R^{9*}$; and $R^{5*}$ is hydrogen, halogen or $C_1$-$C_8$-alkyl; $R^{8*}$ and $R^{9*}$ are independently hydrogen, amino, $C_1$-$C_8$-alkylamino, di($C_1$-$C_8$-alkyl)amino, or $CC_1$-$C_8$-alkyl optionally substituted by hydroxyl; or a pharmaceutically acceptable salt, or solvate thereof, to compositions and use of the compounds in the treatment of diseases ameliorated by inhibition of phosphatidylinositol 3-kinase.

(Ia)

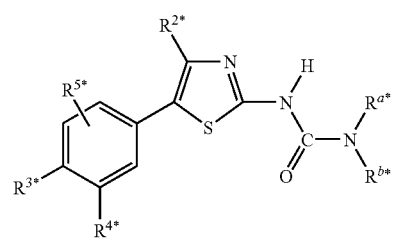

15 Claims, No Drawings

5-PHENYL-THIAZOL-2-YL-UREA DERIVATIVES AND USE AS PI3 KINASE INHIBITORS

The present invention relates to organic compounds, their preparation and their use as pharmaceuticals.

WO 05-21519 describes thiazole derivates having a 2-ureido group substituted by an alkyl or optionally alkyl-substituted alkyl heteroaromatic groups. There exists a need for further pharmaceuticals for use in disorders mediated by pi3 kinase. Ideally, new compounds will have high affinity for pi3 kinase inhibition, selectivity over other receptors, be well absorbed, emonstrate a good or superior pharmacokinetic profile (e.g. have good/stable bioavailability and/or reduced food effect) and be metabolically stable. The compounds will preferably be easy to formulate in one or more suitable dosage forms and also have a reduced side-effect profile.

In a first aspect, the present invention provides compounds of formula I

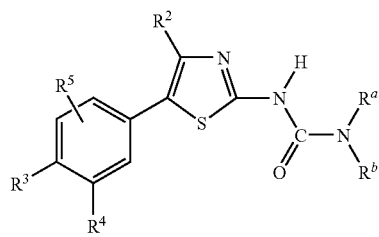

I in free or salt form, suitably a pharmaceutically acceptable salt, or solvate form, wherein:

$R^a$ is hydrogen or $C_1$-$C_4$-alkyl, $R^b$ is $C_1$-$C_8$-fluoroalkyl or $C_1$-$C_8$-hydroxyalkyl substituted by hydroxy or nitrile, $R^3$ is $R^6$, and $R^4$ is hydrogen or $C_1$-$C_8$-haloalkyl, or $R^a$ is hydrogen or $C_1$-$C_4$-alkyl, $R^b$ is $C_1$-$C_8$-fluoroalkyl or $C_1$-$C_8$-hydroxyalkyl substituted by nitrile, $R^3$ is fluoro, and $R^4$ is $R^7$, or $R^a$ is hydrogen or $C_1$-$C_4$-alkyl, $R^b$ is $C_1$-$C_8$-fluoroalkyl or $C_1$-$C_8$-hydroxyalkyl substituted by hydroxy, $R^3$ is fluoro, and $R^4$ is $R^7$, or $R^a$ is hydrogen or $C_1$-$C_4$-alkyl, $R^b$ is $C_1$-$C_8$-fluoroalkyl or $C_1$-$C_8$-hydroxyalkyl substituted by di($C_1$-$C_8$-alkyl)amino, $R^3$ is $R^6$, and $R^4$ is $C_1$-$C_8$-haloalkyl, or $R^a$ is hydrogen or $C_1$-$C_4$-alkyl, $R^b$ is $C_1$-$C_8$-alkyl substituted by —O—$C_1$-$C_8$-alkyl-OH, where one of said alkyl groups on $R^b$ is fluorinated or hydroxylated, $R^3$ is $R^6$, and $R^4$ is fluoro or $C_1$-$C_8$-haloalkyl, or $R^a$ is hydrogen or $C_1$-$C_4$-alkyl, $R^b$ is —CH(CH$_3$)—CH$_2$—OH substituted by at least one fluoro or hydroxy, $R^3$ is $R^6$, and $R^4$ is fluoro, or $R^a$ is hydrogen or $C_1$-$C_4$-alkyl, $R^b$ is $C_1$-$C_8$-alkyl substituted by pyrrolidinyl substituted by $C_1$-$C_8$-fluoroalkyl or $C_1$-$C_8$-hydroxyalkyl, $R^3$ is $R^6$, and $R^4$ is $C_1$-$C_8$-haloalkyl, or $R^a$ is hydrogen or $C_1$-$C_4$-alkyl, $R^b$ is $C_1$-$C_8$-alkyl substituted by oxazolyl substituted by $C_1$-$C_8$-fluoroalkyl or $C_1$-$C_8$-hydroxyalkyl, $R^3$ is $R^6$, and $R^4$ is nitrile or imidazolyl, or $R^a$ is hydrogen or $C_1$-$C_4$-alkyl, $R^b$ is $C_1$-$C_8$-alkyl substituted by isoxazolyl substituted by $C_1$-$C_8$-fluoroalkyl or $C_1$-$C_8$-hydroxyalkyl, $R^3$ is $R^6$, and $R^4$ is $R^7$, or $R^a$ is hydrogen or $C_1$-$C_4$-alkyl, $R^b$ is $C_1$-$C_8$-alkyl substituted by pyrrolyl substituted by $C_1$-$C_8$-fluoroalkyl or $C_1$-$C_8$-hydroxyalkyl, $R^3$ is $R^6$, and $R^4$ is $R^7$, or $R^a$ is hydrogen or $C_1$-$C_4$-alkyl, $R^b$ is $C_1$-$C_8$-alkyl substituted by pyrazolyl substituted by $C_1$-$C_8$-fluoroalkyl or $C_1$-$C_8$-hydroxyalkyl, $R^3$ is $R^6$, and $R^4$ is $R^7$, or $R^a$ is hydrogen or $C_1$-$C_4$-alkyl, $R^b$ is $C_1$-$C_8$-alkyl substituted by —CO—O—CH$_3$, —CO—O-butyl, —CO-di($C_1$-$C_8$-alkyl)amino, —CO—NH$_2$, —NH—CO—$C_1$-$C_8$-alkyl, —SO$_2$—$C_1$-$C_8$-alkyl, —CO—NH—R$^c$, where at least one alkyl group is fluorinated or hydroxylated, where $R^c$ is napthyl, or by —CO—NH—$C_1$-$C_8$-alkyl optionally substituted by di($C_1$-$C_8$-alkyl)-amino, $R^3$ is $R^6$, and $R^4$ is $R^7$, or $R^a$ is hydrogen or $C_1$-$C_4$-alkyl, $R^b$ is —CH(CH$_3$)—CO—NH—$C_1$-$C_8$-alkyl or —CH(CH$_3$)—CO—O—$C_1$-$C_8$-alkyl, where at least one of the alkyl groups is fluorinated or hydroxylated, $R^3$ is $R^6$, and $R^4$ is $R^7$, or $R^a$ is hydrogen or $C_1$-$C_4$-alkyl, $R^b$ is $C_1$-$C_8$-alkyl substituted by —CH(OH)—CH$_2$—OH, where at least one of the alkyl groups is fluorinated or hydroxylated, $R^3$ is $R^6$, and $R^4$ is $R^7$, or $R^a$ is hydrogen or $C_1$-$C_4$-alkyl, $R^b$ is $C_1$-$C_8$-alkyl substituted by $C_1$-$C_8$-alkoxy, where either the alkyl or alkoxy group is fluorinated or hydroxylated, or by —S$C_1$-$C_8$-alkyl, $R^3$ is $R^6$, and $R^4$ is $R^7$, or $R^a$ is hydrogen or $C_1$-$C_4$-alkyl, $R^b$ is $C_1$-$C_8$-alkyl substituted by a 5- or 6-membered heterocyclic ring having three or more ring hetero atoms selected from the group consisting of oxygen, nitrogen and sulphur, that ring being optionally substituted by $C_1$-$C_8$-fluoroalkyl, $C_1$-$C_8$-hydroxyalkyl, —$C_1$-$C_8$-fluoroalkyl-di($C_1$-$C_8$-alkyl)amino, —$C_1$-$C_8$-hydroxyalkyl-di($C_1$-$C_8$-alkyl)amino, or by $C_3$-$C_8$-cycloalkyl, $R^3$ is $R^6$, and $R^4$ is $R^7$, or $R^a$ is hydrogen or $C_1$-$C_4$-alkyl, $R^b$ is $C_1$-$C_8$-alkyl substituted by oxazolyl substituted by $C_3$-$C_8$-fluoroalkyl or $C_3$-$C_8$-hydroxyalkyl, $R^3$ is $R^6$, and $R^4$ is $R^7$, or $R^a$ is hydrogen or $C_1$-$C_4$-alkyl, $R^b$ is $C_1$-$C_8$-alkyl substituted by imidazolyl substituted by $C_1$-$C_8$-fluoroalkyl or $C_1$-$C_8$-hydroxyalkyl optionally substituted by hydroxy or $C_1$-$C_8$-alkoxy, $R^3$ is $R^6$, and $R^4$ is $R^7$, or $R^a$ is hydrogen or $C_1$-$C_4$-alkyl, $R^b$ is $C_1$-$C_8$-alkyl substituted by —CO-Het where Het is a 5- or 6-membered heterocyclic ring having two or more ring hetero atoms selected from the group consisting of oxygen, nitrogen and sulphur, that ring being optionally substituted by $C_1$-$C_8$-haloalkyl or $C_1$-$C_8$-hydroxyalkyl, $R^3$ is $R^6$, and $R^4$ is $R^7$, or $R^a$ is hydrogen or $C_1$-$C_4$-alkyl, $R^b$ is an aza-bicyclo[3.2.1]oct-3-yl ring optionally substituted by $C_1$-$C_8$-fluoroalkyl or $C_1$-$C_8$-hydroxyalkyl, $R^3$ is $R^6$, and $R^4$ is $R^7$;

$R^2$ is $C_1$-$C_4$-alkyl or halogen;

$R^5$ is hydrogen, halogen or $C_1$-$C_8$-alkyl;

$R^6$ is halo, —SO$_2$—CH$_3$, —SO$_2$—CF$_3$, carboxy, —CO—NH$_2$, —CO-di($C_1$-$C_8$-alkyl)amino, or a 5- or 6-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino;

$R^7$ is hydrogen, halo, —SO$_2$CH$_3$, nitrile, $C_1$-$C_8$-haloalkyl, imidazolyl, $C_1$-$C_8$-alkyl, —NR$^8$R$^9$, or —SO$_2$—NR$^8$R$^9$; and $R^8$ and $R^9$ are independently hydrogen, amino, $C_1$-$C_8$-alkylamino, di($C_1$-$C_8$-alkyl)amino, or $C_1$-$C_8$-alkyl optionally substituted by hydroxy, or $R^8$ and $R^9$ together form a 5- to 10-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino, where said 5- or 6-membered heterocyclic ring is optionally substituted by one or more substituents selected from groups (i) or (ii), where (i) is selected from halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, and $C_1$-$C_8$-alkyl optionally substituted by hydroxy, $C_1$-$C_8$-alkoxy and di($C_1$-$C_8$-alkyl)amino, or (ii) is selected from halo, oxo, $C_3$-$C_5$-cycloalkyl, and $C_1$-$C_4$-alkyl optionally substituted by hydroxy, $C_1$-$C_4$-alkoxy, $C_1$-$C_8$-alkylamino and di($C_1$-$C_4$-alkyl)amino, and where said 5- to 10-membered heterocyclic ring is optionally substituted by one or more substituents selected from either group (i) or group (ii) where group (i) is selected from halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino, and group (ii) is selected from $C_1$-$C_4$-alkyl.

Terms used in the specification have the following meanings:

"Halogen" or "halo" may be fluorine, chlorine, bromine or iodine.

Alkyl, alkenyl, alkynyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups.

"$C_1$-$C_8$-haloalkyl" denotes $C_1$-$C_8$-alkyl as hereinbefore defined substituted by one or more halogen atoms as hereinbefore defined.

"Aminocarbonyl" as used herein denotes amino attached through the nitrogen atom to a carbonyl group.

"$C_1$-$C_8$-alkylcarbonyl" and "$C_1$-$C_8$-alkoxycarbonyl" denote $C_1$-$C_8$-alkyl and $C_1$-$C_8$-alkoxy respectively as hereinbefore defined attached by a carbon atom to a carbonyl group.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different.

"5- or 6-membered or 5- to 10-membered heterocyclic rings containing at least one ring heteroatom selected from the group consisting of nitrogen, oxygen and sulphur" as used herein may be, for example, furan, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperazine, morpholino, triazine, oxazine or thiazole. Heterocyclic rings having aromatic bonds may be described as heteroaryl groups.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of the present invention include compounds of formula I in free or salt form, wherein:

$R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by hydroxy or nitrile, $R^3$ is $R^6$, and $R^4$ is hydrogen or $C_1$-$C_8$-haloalkyl, or $R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by nitrile, $R^3$ is fluoro, and $R^4$ is $R^7$, or $R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by hydroxy, $R^3$ is fluoro, and $R^4$ is $R^7$, or $R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by di($C_1$-$C_8$-alkyl)amino, $R^3$ is $R^6$, and $R^4$ is $C_1$-$C_8$-haloalkyl, or $R^a$ is hydrogen, $R^b$ is 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by —O—$C_1$-$C_8$-alkyl-OH, $R^3$ is $R^6$, and $R^4$ is fluoro or $C_1$-$C_8$-haloalkyl, or $R^a$ is hydrogen, $R^b$ is $C_1$-$C_8$-alkyl substituted by pyrrolidinyl substituted by $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, $R^3$ is $R^6$, and $R^4$ is $C_1$-$C_8$-haloalkyl, or $R^a$ is hydrogen, $R^b$ is $C_1$-$C_8$-alkyl substituted by oxazolyl substituted by $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, $R^3$ is $R^6$, and $R^4$ is nitrile or imidazolyl, or $R^a$ is hydrogen, $R^b$ is $C_1$-$C_8$-alkyl substituted by isoxazolyl substituted by $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, $R^3$ is $R^6$, and $R^4$ is $R^7$, or $R^a$ is hydrogen, $R^b$ is $C_1$-$C_8$-alkyl substituted by pyrrolyl substituted by $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, $R^3$ is $R^6$, and $R^4$ is $R^7$, or $R^a$ is hydrogen, $R^b$ is $C_1$-$C_8$-alkyl substituted by pyrazolyl substituted by $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, $R^3$ is $R^6$, and $R^4$ is $R^7$, or $R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by —CO—O—$CH_3$, —CO—O-butyl, —CO-di($C_1$-$C_8$-alkyl)amino, —CO—$NH_2$, —NH—CO—$C_1$-$C_8$-alkyl, —$SO_2$—$C_1$-$C_8$-alkyl, —CO—NH—$R^c$ where $R^c$ is napthyl, or by —CO—NH—$C_1$-$C_8$-alkyl optionally substituted by di($C_1$-$C_8$-alkyl) amino, $R^3$ is $R^6$, and $R^4$ is $R^7$, or $R^a$ is hydrogen, $R^b$ is $C_1$-$C_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by —CH(OH)—CH$_2$—OH, R$^3$ is R$^6$, and R$^4$ is R$^7$, or R$^a$ is hydrogen, R$^b$ is C$_1$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, substituted by C$_1$-C$_8$-alkoxy, or by —SC$_1$-C$_8$-alkyl, R$^3$ is R$^6$, and R$^4$ is R$^7$, or R$^a$ is hydrogen, R$^b$ is C$_1$-C$_8$-alkyl substituted by a 5- or 6-membered heterocyclic ring having three or more ring hetero atoms selected from the group consisting of oxygen, nitrogen and sulphur, that ring being optionally substituted by C$_1$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, —C$_1$-C$_8$-alkyl-di(C$_1$-C$_8$-alkyl)amino, or by C$_3$-C$_8$-cycloalkyl, R$^3$ is R$^6$, and R$^4$ is R$^7$, or R$^a$ is hydrogen, R$^b$ is C$_1$-C$_8$-alkyl substituted by oxazolyl substituted by C$_2$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, R$^3$ is R$^6$, and R$^4$ is R$^7$, or R$^a$ is hydrogen, R$^b$ is C$_1$-C$_8$-alkyl substituted by imidazolyl substituted by C$_1$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, optionally substituted by hydroxy or C$_1$-C$_8$-alkoxy, R$^3$ is R$^6$, and R$^4$ is R$^7$, or R$^a$ is hydrogen, R$^b$ is C$_1$-C$_8$-alkyl substituted by —CO-Het where Het is a 5- or 6-membered heterocyclic ring having two or more ring hetero atoms selected from the group consisting of oxygen, nitrogen and sulphur, that ring being optionally substituted by C$_1$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl, R$^3$ is R$^6$, and R$^4$ is R$^7$, or R$^a$ is hydrogen, R$^b$ is an aza-bicyclo[3.2.1]oct-3-yl ring optionally substituted by C$_1$-C$_8$-fluoroalkyl, e.g. 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl R$^3$ is R$^6$, and R$^4$ is R$^7$;

R$^2$ is C$_1$-C$_4$-alkyl or halogen;
R$^5$ is hydrogen;
R$^6$ is halo or —SO$_2$—CH$_3$; and
R$^7$ is hydrogen, halo, —SO$_2$CH$_3$, nitrile, C$_1$-C$_8$-haloalkyl or imidazolyl.

According to formula (I), preferably, R$^a$ is H.

According to formula (I), preferably, R$^b$ is —(C$_1$-C$_4$-alkylene)-Y—C$_1$-C$_4$-fluoroalkyl, where Y represents a —CONH— or a five membered heteroaryl group. C$_1$-C$_4$-alkylene is suitably ethylene. C$_1$-C$_4$-fluoroalkyl is suitably 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl. Where Y is a five membered heteroaryl group, Y is suitably selected from imidazolyl or tetrazolyl, preferably tetrazolyl. Preferably, Y is CONH or a 2,5-substituted tetrazolyl.

According to formula (I), preferably, R$^2$ is C$_1$-C$_4$-alkyl, most preferably methyl.

According to formula (I), preferably, R$^3$ is —SO$_2$—CH$_3$.
According to formula (I), preferably, R$^4$ is fluoro.
According to formula (I), preferably, R$^5$ is hydrogen.

A suitable sub-formula of formula (I) may be represented by formula (Ia)

(Ia)

wherein: R$^{a*}$ is hydrogen or C$_1$-C$_4$-alkyl;
R$^{b*}$ is —(C$_1$-C$_4$-alkylene)-Y—C$_1$-C$_4$-fluoroalkyl or —(C$_1$-C$_4$-alkylene)-Y—C$_1$-C$_4$-hydroxyalkyl;
Y represents —CONH— or a five membered heteroaryl group.
R$^{2*}$ is C$_1$-C$_4$-alkyl or halogen;
R$^{3*}$ is halo, —SO$_2$—CH$_3$, —SO$_2$—CF$_3$, carboxy, —CO—NH$_2$, —CO-di(C$_1$-C$_8$-alkyl)amino, or a 5- or 6-membered heterocyclic ring having one or more ring hetero atoms selected from the group consisting of oxygen, nitrogen and sulphur, that ring being optionally substituted by halo, cyano, oxo, hydroxy, carboxy, nitro, C$_3$-C$_8$-cycloalkyl, C$_1$-C$_8$-alkylcarbonyl, C$_1$-C$_8$-alkoxy optionally substituted by aminocarbonyl, or C$_1$-C$_8$-alkyl optionally substituted by hydroxy, C$_1$-C$_8$-alkoxy, C$_1$-C$_8$-alkylamino or di(C$_1$-C$_8$-alkyl)amino;
R$^{4*}$ is hydrogen, halo, —SO$_2$—CH$_3$, nitrile, C$_1$-C$_8$-haloalkyl, imidazolyl, C$_1$-C$_8$-alkyl, —NR$^{8*}$R$^{9*}$, or —SO$_2$—NR$^{8*}$R$^{9*}$; and
R$^{5*}$ is hydrogen, halogen or C$_1$-C$_8$-alkyl;
R$^{8*}$ and R$^{9*}$ are independently hydrogen, amino, C$_1$-C$_8$-alkylamino, di(C$_1$-C$_8$-alkyl)amino, or C$_1$-C$_8$-alkyl optionally substituted by hydroxyl; or a suitable salt, suitably a pharmaceutically acceptable salt, or solvate thereof.

A further suitable sub-formula of formula (I) may be represented by formula (Ib)

(Ib)

wherein
R$^{a**}$ is H;
R$^{b**}$ is —(C$_1$-C$_4$-alkylene)-Y—C$_1$-C$_4$-fluoroalkyl;
Y represents a —CONH— or a five membered heteroaryl group;
R$^{2**}$ is C$_1$-C$_4$-alkyl;
R$^{3**}$ is —SO$_2$—CH$_3$;
R$^{4**}$ is fluoro; and
R$^{5**}$ is hydrogen, or a suitable salt, suitably a pharmaceutically acceptable salt, or solvate thereof.

A suitable compound of the present invention is selected from:
N-(2-Fluoro-1,1-dimethyl-ethyl-3-{3-[5-(3-fluoro-4-methanesulfonyl-phenyl)-4-methyl-thiazol-2-yl]-ureido}-propionamide;

N-(2,2-Difluoroethyl)-3-{3-[5-(3-fluoro-4-methanesulfo-nyl-phenyl)-4-methyl-thiazol-2-yl]-ureido}-propiona-mide;

1-[5-(3-Fluoro-4-methanesulfonyl-phenyl)-4-methyl-thia-zol-2-yl]-3-{2-[1-(3,3,3-trifluoro-propyl)-1H-imidazol-4-yl]-ethyl}-urea;

1-{2-[1-(2-Fluoro-ethyl)-1H-imidazol-4-yl]-ethyl}-3-[5-(3-fluoro-4-methanesulfonyl-phenyl)-4-methyl-thiazol-2-yl]-urea;

1-{2-[2-(2-Fluoro-ethyl)-2H-tetrazol-5-yl]-ethyl}-3-[5-(3-fluoro-4-methanesulfonyl-phenyl)-4-methyl-thiazol-2-yl]-urea;

N-(2-Fluoro-ethyl)-3-{3-[5-(3-fluoro-4-methanesulfonyl-phenyl)-4-methyl-thiazol-2-yl]-ureido}-propionamide;

3-(3-[5-(3-Fluoro-4-methanesulfonyl-phenyl)-4-methylthi-azol-2-yl]-ureido)-N-(2,2,2-trifluoro-1,1-dimethyl-ethyl)-propionamide;

3-{3-[5-(3-Fluoro-4-methanesulfonyl-phenyl)-4-methyl-thiazol-2-yl]-ureido}-N-(2,2,2-trifluoro-ethyl)-propiona-mide; or a suitable salt, suitably a pharmaceutically accept-able salt, or solvate thereof.

Many of the compounds represented by formula I are capable of forming acid addition salts, particularly pharma-ceutically acceptable acid addition salts. Pharmaceutically acceptable acid addition salts of the compound of formula I include those of inorganic acids, for example, hydrohalic acids such as hydrofluoric acid, hydrochloric acid, hydrobro-mic acid or hydroiodic acid, nitric acid, sulfuric acid, phos-phoric acid; and organic acids, for example aliphatic mono-carboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlo-robenzoic acid, diphenylacetic acid or triphenylacetic acid, aromatic hydroxy acids such as o-hydroxybenzoic acid, p-hy-droxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. car-boxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In a second aspect, the present invention provides a process for preparing a compound of formula I in free or salt form wherein $R^2$, $R^3$, $R^4$, $R^5$, $R^a$ and $R^b$ are as hereinbefore defined, which process comprises the steps of:

(i) (A) reacting a compound of formula II

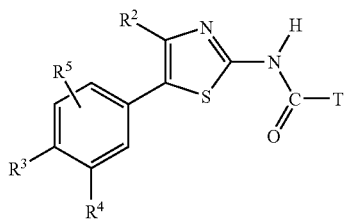

wherein $R^2$, $R^3$, $R^4$ and $R^5$ are hereinbefore defined and T is a 5- or 6-membered heterocyclic ring having one or more ring hetero atoms selected from the group consist-ing of oxygen, nitrogen and sulphur, with a compound of formula III

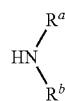

wherein $R^a$ and $R^b$ are hereinbefore defined;

(B) reacting compounds of formula IV

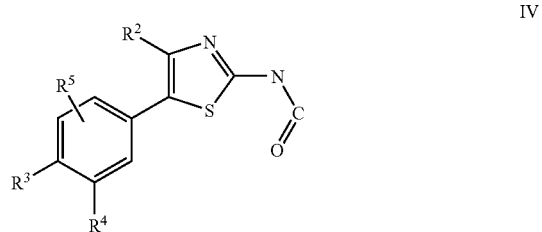

wherein $R^2$, $R^3$, $R^4$ and $R^5$ are hereinbefore defined with a compound of formula III wherein $R^a$ and $R^b$ are herein-before defined;

(C) for the preparation of compounds of formula I where $R^a$ is hydrogen and $R^2$, $R^3$, $R^4$, $R^5$ and $R^b$ are as herein-before defined, reacting a compound of formula V

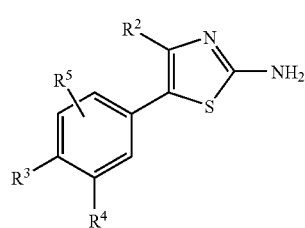

wherein $R^2$, $R^3$, $R^4$ and $R^5$ are hereinbefore defined, with a compound of formula VI

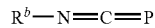

wherein $R^b$ is as hereinbefore defined; or (D) for the preparation of compounds of formula I where $R^a$ is hydrogen, $R^b$ is $C_1$-$C_8$-alkyl substituted by imida-zolyl substituted by $C_1$-$C_8$-alkyl optionally substituted by hydroxy or $C_1$-$C_8$-alkoxy and $R^2$, $R^3$, $R^4$ and $R^5$ are as hereinbefore defined, reacting a compound of formula V where $R^2$, $R^3$, $R^4$ and $R^5$ are hereinbefore defined, with a compound of formula VII

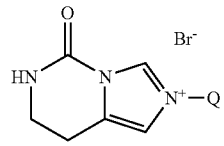

where Q is $C_1$-$C_8$-alkyl optionally substituted by hydroxy or $C_1$-$C_8$-alkoxy; and (ii) recovering the resultant compound of formula I in free or salt form.

Process variant (A) may be carried out using known procedures for reacting carbonyl di-heterocyclic intermediates (e.g. acylimidazolides when T is imidazole) with amines to form ureas, or analogously, e.g. as hereinafter described in the Examples. The reaction may be carried out in an organic solvent, e.g. dimethylformamide (DMF) or dioxane, in the presence or absence of a base, for example triethylamine or sodium hydride. The reaction temperature may be from about 10° C. to about 100° C., but conveniently room temperature.

Process variant (B) may be carried out using known procedures for reacting isocyanates with amines, or analogously, e.g. as hereinafter described in the Examples. The reaction may be carried out in an organic solvent, e.g. dioxane or DMF. The reaction temperature may be an elevated temperature, for example from 50° C. to 100° C., but preferably about 80° C.

Process variants (C) may be carried out using known procedures for reacting isocyanates with amines, or analogously, e.g. as hereinafter described in the Examples. The reaction may be carried out in an organic solvent, e.g. dioxane or DMF. The reaction temperature may be an elevated temperature, for example from 50° C. to 100° C., but preferably about 80° C.

Process variant (D) may be carried out using known procedures for reacting 2-alkyl-5-oxo-5,6,7,8-tetrahydro-imidazo[1,5-c]pyrimidin-2-ium compounds with 2-amino-5-phenyl-thiazoles, or analogously, e.g. as hereinafter described in the Examples. The reaction may be carried out in an organic solvent, e.g. DMF, in the presence of a base, e.g. triethylamine. The reaction temperature may be 100-170° C., but conveniently about 120° C.

Compounds of formula II or formula IV may be prepared by reacting a compound of formula V wherein $R^2$, $R^3$, $R^4$ and $R^5$ are as hereinbefore defined with a compound of formula VIII

VIII wherein each T, which may be the same or different, is a 5- or 6-membered heterocyclic ring having one or more ring hetero atoms selected from the group consisting of oxygen, nitrogen and sulphur, using known procedures, or analogously, e.g. as described in the Examples. The compound of formula VIII is preferably 1,1'-carbonyldiimidazole (CDI). The reaction may be carried out in an organic solvent, e.g. dichloromethane (DCM). The reaction temperature may be from 20° C. to the reflux temperature of the solvent, but conveniently about 40° C.

Compounds of formula IV may also be prepared by reacting a compound of formula V wherein $R^2$, $R^3$, $R^4$ and $R^5$ are as hereinbefore defined, with phosgene, using known procedures, or analogously, e.g. as described in the Examples.

Compounds of formula III are commercially available or may be prepared by known methods, or analogously, e.g. as described in the Examples.

Compounds of formula V may be prepared by reacting a compound of formula IX

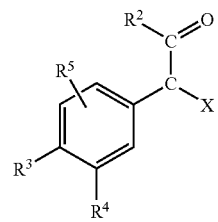

IX wherein $R^2$, $R^3$, $R^4$ and $R^5$ are as hereinbefore defined and X is a halogen, with thiourea, or analogously, using known procedures for preparing aminothiazoles. For example as described in the Examples below or as described in European patent specification EP 117082A. The reaction may be carried out in an organic solvent, e.g. an alcohol such as ethanol. The reaction temperature may be from room temperature to the reflux temperature of the solvent, but conveniently from about 50° C. to about 70° C.

Compounds of formula V where $R^2$, $R^3$, $R^4$ and $R^5$ are as hereinbefore defined, may also be prepared by hydrolysing a compound of formula X

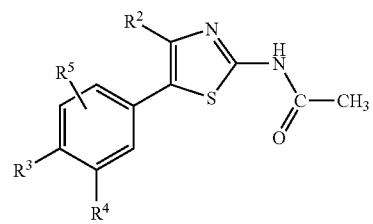

X where $R^2$, $R^3$, $R^4$ and $R^5$ are as hereinbefore defined, using aqueous sodium hydroxide or hydrochloric acid solution at temperatures of 50° C. to the reflux temperature of the solvent. A co-solvent, preferably ethanol may be added to aid solubility of the starting material.

Compounds of formula VI are commercially available or may be prepared by known methods, or analogously, e.g. as described in the Examples.

Compounds of formula VII may be prepared by known methods, for example as described in R. Jain and L. A. Cohen, *Tetrahedron* (1996), 52, p 5363-5370.

Compounds of formula VIII are commercially available or may be prepared by known methods, or analogously, e.g. as described in the Examples.

Compounds of formula IX are commercially available or may be prepared by reacting a compound of formula XI

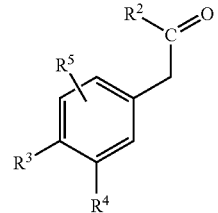

XI wherein $R^2$, $R^3$, $R^4$ and $R^5$ are as hereinbefore defined, with a halogenating agent, for example bromine, or analogously, e.g. as described in the Examples.

Compounds of formula X, where $R^3$ is —$SO_2CH_3$, $R^4$ is $NR^8R^9$ and $R^2$ and $R^5$ are as hereinbefore defined, may be prepared from compounds of formula IX where $R^3$ is $SO_2CH_3$, $R^4$ is a halogen, preferably fluorine, and $R^2$ and $R^5$ are as hereinbefore defined, using known procedures for reacting aryl halides, ortho to an electron withdrawing group, with primary or secondary amines, or analogously, e.g. as hereinafter described in the Examples. The reaction may be carried out either neat or in an organic solvent, e.g. dimethylsulphoxide. The reaction temperature may be from 100° C. to 170° C. but conveniently about 120° C. to 140° C.

Compounds of formula X, where $R^3$ is —$SO_2CH_3$, and $R^2$, $R^4$ and $R^5$ are as hereinbefore defined, may be prepared from compounds of formula X, where $R^3$ is —$SO_2Cl$ and $R^2$, $R^4$ and $R^5$ are as hereinbefore defined, using the procedure known in R. W. Brown, *J. Org. Chem.*, (1991), 56, 4974 for converting sulfonyl halides to sulfones, or analogously, e.g. as hereinafter described in the Examples. The procedure may be carried out using an alkali metal sulphite, e.g. sodium sulphite, and an alkali metal bicarbonate, e.g. sodium bicarbonate, in water at a temperature from 20° C. to 100° C., but conveniently at about 75° C. The reaction with bromoacetic acid may be carried out at temperature from 50° C. to 150° C., but conveniently at about 100° C. An alkyl halide, e.g. iodomethane may be used in place of bromoacetic acid.

Compounds of formula X where $R^2$, $R^3$, $R^4$ and $R^5$ are as hereinbefore defined, may be prepared from compounds of formula IX, where $R^2$, $R^3$, $R^4$ and $R^5$ are as hereinbefore defined, as described analogously for the preparation of compounds of formula V, where $R^2$, $R^3$, $R^4$ and $R^5$ are as hereinbefore defined, but using N-acetyl thiourea instead of thiourea.

Compounds of formula X, where $R^3$ is —$SO_2$—Cl and $R^2$, $R^4$ and $R^5$ are as hereinbefore defined, may be prepared by reacting compounds of formula X, where $R^3$ is —$NH_2$ and $R^2$, $R^4$ and $R^5$ are as hereinbefore defined, with nitrous acid to give a diazo compound which is then reacted with sulphur dioxide in the presence of copper chloride, for example by the method described in E. E. Gilbert, *Synthesis* (1969), 1-10, to give the corresponding sulfonyl chlorides.

Compounds of formula X, where $R^3$ is —$NH_2$ and $R^2$, $R^4$ and $R^5$ are as hereinbefore defined, may be prepared by reduction of compounds of formula X, where $R^3$ is —$NO_2$ and $R^2$, $R^4$ and $R^5$ are as hereinbefore defined using standard techniques known for the reduction of aromatic nitro compounds to anilines, for example catalytic hydrogenation using a transition metal catalyst, preferably palladium on carbon, in an organic solvent, e.g. ethyl acetate, under an atmosphere of hydrogen.

Compounds of formula X, where $R^3$ is —$NO_2$ and $R^2$, $R^4$ and $R^5$ are as hereinbefore defined are prepared by known procedures, for example as described in J. Liebscher, E. Mitzner, *Synthesis,* (1985), 4, 414-417.

Compounds of formula XI are commercially available or may be prepared from compounds of formula XII

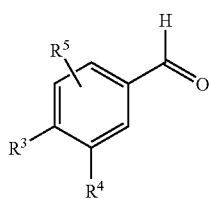

XII where $R^3$, $R^4$ and $R^5$ are as hereinbefore defined, using the method described in R. V. Heinzelman, *Org. Synth.* (1963), IV, 573, or analogously, e.g. as described in the Examples.

Compounds of formula XI where $R^3$ is halo, $R^4$ is —$SO_2CH_3$ and $R^2$ and $R^5$ are as hereinbefore defined may be prepared from a compound of formula XI where $R^3$ is halo, $R^4$ is hydrogen and $R^2$ and $R^5$ are as hereinbefore defined, using standard procedures e.g. treatment with chlorosulfonic acid followed by reduction with sodium sulfite using the procedure known in R. W. Brown, *J. Org. Chem.*, (1991), 56, 4974 for converting sulfonyl halides to sulfones, or analogously, e.g. as hereinafter described in the Examples. The reduction may be carried out with an alkali metal sulphite, e.g. sodium sulphite, and the alkali metal bicarbonate, e.g. sodium bicarbonate in water at a temperature from 20° C. to 100° C., but conveniently at about 75° C. followed by alkylation with methyl iodide.

Compounds of formula XII are commercially available or may be prepared by known methods, or analogously, e.g. as described in the Examples.

Compounds of formula XII where $R^3$ is —$SO_2CH_3$ and $R^4$ and $R^5$ are as hereinbefore defined may be prepared from compounds of formula XII where $R^3$ is halo and $R^4$ and $R^5$ are as hereinbefore defined, for example by the method described by A. Ulman and E. Urankar in *J. Org. Chem.*, (1989), 54, p 4691-4692, or analogously, e.g. as described in the Examples.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I and their pharmaceutically acceptable salts, hereinafter referred to alternatively as agents of the invention, are useful as pharmaceuticals. In particular, they exhibit inhibition of phosphatidylinositol 3-kinase (Pi3 kinase) enzymes, especially the gamma isoform (p110?), which are responsible for generating phosphorylated signalling products. The inhibitory properties of compounds of formula I may be demonstrated in the following test procedures:

Baculovirus expressing different fragments of PI3K? fused to GST have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.,* 324:489. Residues 38-1102 of human PI3K? are subcloned into the BamH1 and EcoR1 sites of the transfer vector pAcG2T (Pharmingen) to create a GST-PI3K? lacking the first 37 residues of PI3K?. To express the recombinant protein, Sf9 (*Spodoptera frugiperda* 9) insect cells are routinely maintained at densities between $3\times10^5$ and $3\times10^6$ cells/ml in serum containing TNMFH medium (Sigma). Sf9 cells, at a density of $2\times10^6$ are infected with human GST-PI3K?? 34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1\times10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FAL- CON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 µl test compound in 5% dimethylsulphoxide and 20 µl assay mix (40 mM Tris, 200 mM NaCl, 2 mM ethyleneglycol-aminoethyl-tetraacetic acid (EGTA), 15 µg/ml phosphatidylinositol, 12.5 µM adenosine triphosphate (ATP), 25 mM MgCl$_2$, 0.1 µCi [$^{33}$P]ATP). The reaction is started by the addition of 20 µl of enzyme mix (40 mM Tris, 200 mM NaCl, 2 mM EGTA containing recombinant GST-p110?). The plate is incubated at room temperature for 60 minutes and the reaction terminated by the adding 150 µl of WGA-bead stop solution (40 mM Tris, 200 mM NaCl, 2 mM EGTA, 1.3 mM ethylene diamine tetraacetic acid (EDTA), 2.6 µM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 µl of 5% dimethylsulphoxide (DMSO) and non-specific activity is determined by adding 10 µl 50 mM EDTA in place of the test compound.

Compounds of the Examples hereinbelow have IC$_{50}$ (?) values between 0.01-0.25 µM in the aforementioned assay or demonstrate selectivity with respect to the ?, a, d or β isoform as determined by a corresponding assay.

The superior properties of the compounds of the present invention may be demonstrated by the comparison of their activities with the corresponding non-fluorinated compounds described in WO0521519. For example, the relative activities of Examples of the present invention against equivalent non-fluorinated derivatives are shown in the following table:

| Ex. | R$^b$ | IC$_{50}$ µM (?) | IC$_{50}$ Non fluorinated µM (?) |
|---|---|---|---|
| 1 | H₃C–CH(CH₃)–CH₂F with NH–C(O)–propyl | 0.046 | 0.085 |
| 2 | CHF₂–CH₂–NH–C(O)–propyl | 0.028 | 0.123 |
| 7 | imidazole-N-CH₂CH₂F, 4-propyl | 0.028 | 0.078 |
| 8 | triazole-N-CH₂CH₂F, 5-propyl | 0.010 | 0.045 |

Thus, for example, the compound of Ex 8 of the present invention exhibits approximately a four-fold increase in activity over the corresponding compound described in WO0521519.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyper-reactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyper-reactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, cystic fibrosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrhoeal diseases, ischemial/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or antitussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/ PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially the compound 5-[(R)-2-(5,6-Diethyl-indan-2-ylamino)-1-hydroxy-ethyl]-8-hydroxy-1H-quinolin-2-one, and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodeling.

Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Agents of the invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves opthalmopathy, alopecia greata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Agents of the invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used, in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-yanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxyphenyl)-amino-6,7-dimethoxyquinazoline] (WHI-P154), [4-(3', 5'-dibromo-4'-hydroxyphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a SIP receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-(4-[1-(4-cyclohexyl-3-trifluoromethyl-benzyloxyimino)-ethyl]-2-ethyl-benzyl)-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The agents of the invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The agents of the invention may also be used in the treatment of anemia, according to WO2006/040318.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula I either dissolved, or suspended, in a vehicle containing water, a cosolvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Abbreviations used are as follows: rt is room temperature, CDI is 1,1'-carbonyldiimidazole, DCM is dichloromethane, DIPEA is diisopropylethylamine, DMF is Dimethylformamide, THF is tetrahydrofuran, HPLC is High Performance Liquid Chromatography, DMF-DMA is NAN-Dimethylformamide dimethylacetal, DMSO is dimethyl sulfoxide, HCl is Hydrochloric acid, TFA is Trifluoroacetic acid. HOBT is Hydroxy benzotriazole, and HOAt is Hydroxy azabenzotriazole.

Preparation of Intermediates

The following aminothiazole intermediates of formula (A)

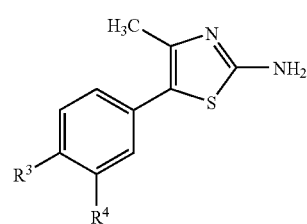

A are shown in Table 1 below, their method of preparation being described hereinafter.

TABLE 1

| Intermediate | $R^3$ | $R^4$ | M/s MH+ |
|---|---|---|---|
| AA | —$SO_2CH_3$ | F | 287.11 |

Intermediate AA

5-(3-Fluoro-4-methanesulfonyl-phenyl)-4-methyl-thiazol-2-ylamine

AA1) 3-Fluoro-4-methanesulfonyl-benzaldehyde

Methane sulfinic acid sodium salt (20.1 g, 200 mmol) was added to a stirred solution of 3,4-difluorobenzaldehyde (22.5 g, 158 mmol) in dry DMSO (200 ml) at 75° C. After 2 hours the reaction was poured onto ice-water (200 ml). The precipitate was filtered, washed with water and dissolved in chloroform (400 ml). The organic extract was washed with water (2×200 ml), dried over MgSO$_4$, filtered, and the solvent removed to give the title compound as a white solid.

AA2) 2-Fluoro-1-methanesulfonyl-4-(2-nitropropenyl)-benzene

A stirred mixture of 3-fluoro-4-methanesulfonyl-benzaldehyde (Example AA1) (24 g, 0.119 mol), nitroethane (70 ml, 0.97 mol) and ammonium acetate (2.75 g, 35 mmol) was heated at reflux under argon for 24 hours. The mixture was concentrated to give an oil which was dissolved in chloroform (200 ml) and washed with water (2×200 ml), followed by brine (100 ml). The organic extract was dried (MgSO$_4$), filtered and the solvent removed to give the product as an orange oil. This was used immediately in the next step.

AA3) 1-(3-Fluoro-4-methanesulfonyl-phenyl)-propan-2-one

Iron powder (25 g, 0.45 mol) was added to a stirred mixture of freshly prepared 2-fluoro-1-methanesulfonyl-4-(2-nitropropenyl)-benzene (Example AA2) (29 g, 0.112 mol) in THF (50 ml). Water (110 ml) was added and the mixture is heated to 60° C. Concentrated hydrochloric acid (50 ml) was added slowly over 1 h at 60-90° C. The reaction was then stirred at 100° C. for 20 hours then diluted with cold water (500 ml) and filtered through Celite™ filter material washing with chloroform (500 ml). The organic extract was washed with water (200 ml) followed by brine (200 ml). After drying (MgSO$_4$) the mixture was absorbed on silica and purified by chromatography, eluting with hexane-ethyl acetate (1:1) to give the titled compound.

AA4) 5-(3-Fluoro-4-methanesulfonyl-phenyl)-4-methyl-thiazol-2-ylamine 1-(3-Fluoro-4-methanesulfonyl-phenyl)-propan-2-one (AA3) (1.0 g, 4.34 mmol) was dissolved in dioxane (35 ml) and the solution was cooled to 10° C. at which point the mixture was semi frozen. Bromine (0.201 ml, 3.6 mmol, 0.8 eq.) was added slowly and the mixture stirred for an additional 15 min in a semi frozen state. The mixture was then allowed to warm to room temperature and the solvent removed to give a brown oil containing starting material and 1-bromo-1-(3-fluoro-4-methanesulfonyl-phenyl)-propan-2-one. This material was dissolved in ethanol (30 ml) and thiourea (0.236 g, 3.1 mmol) was added in one portion. The mixture was stirred at 60° C. for 30 minutes then allowed to cool whereupon the product crystallised. Filtration afforded the hydrobromide salt of the product as a white solid. The free base was prepared by dissolving the hydrobromide salt in dilute aqueous hydrochloric acid and adding sodium hydroxide solution until alkaline. The title compound precipitated as the free base.

The following imidazole-urea intermediates of formula (B)

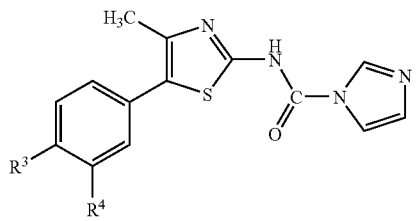

are shown in the Table 2 below, the method of preparation being described hereinafter.

TABLE 2

| Intermediate | R$^3$ | R$^4$ | Starting material | Method |
|---|---|---|---|---|
| BA | —SO$_2$CH$_3$ | F | AA | Ba |

Preparation of Imidazole-1-carboxylic acid [5-(3-fluoro-4-methanesulfonyl-phenyl)-4-methyl-thiazol-2-yl]-amide A suspension of 5-(3-Fluoro-4-methanesulfonyl-phenyl)-4-methyl-thiazol-2-ylamine (17.5 mmol) and 1,1'-carbonyldiimidazole (4.26 g, 26.3 mmol, 1.5 equivalents) in CH$_2$Cl$_2$ (100 ml) was heated at 40° C.-reflux under argon until no starting material remains (30 min-5 hours) as determined by HPLC and NMR. When cool the solid precipitate was removed by filtration.

This solid consisted of the imidazole-urea intermediate (B) together with variable amounts of the corresponding isocyanate and imidazole which resulted from reversible thermal elimination of imidazole under the reaction conditions. This solid was used in the subsequent steps since the imidazole-urea intermediate and isocyanate intermediate were equally suitable as precursors to ureas.

The following amine intermediates of formula C, H$_2$N(CH$_2$)$_2$Het, where Het is

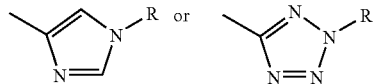

are shown in the Table 3 below, the method of preparation being described hereinafter.

TABLE 3

| Intermediate | R |
|---|---|
| C1 | —CH$_2$CH$_2$F |
| C2 | —CH$_2$CH$_2$F |

Intermediate C1

2-[1-(2-Fluoro-ethyl)-1H-imidazol-4-yl]-ethylamine dihydrochloride

Step 1: 2-(2-Fluoro-ethyl)-5-oxo-5,6,7,8-tetrahydro-imidazo[1,5-c]pyrimidin-2-ium bromide 7,8-Dihydro-6H-imidazo[1,5-c]pyrimidin-5-one (0.45 g, 3.28 mmol) was suspended in acetonitrile (4 ml) and 1-bromo-2-fluoroethane (0.326 ml, 4.38 mmol) added. The reaction mixture was heated in a microwave reactor at 160° C.

for 1 hour, then the solvent evaporated and the crude reaction mixture purified by silica chromatography eluting with dichloromethane:methanol 9:1 to afford the titled compound.
Step 2: 2-[1-(2-Fluoro-ethyl)-1H-imidazol-4-yl]-ethylamine dihydrochloride A solution of 2-(2-Fluoro-ethyl)-5-oxo-5,6,7,8-tetrahydro-imidazo[1,5-c]pyrimidin-2-ium bromide (0.64 g, 2.42 mmol) in aqueous 6 M HCl, was heated at 130° C. for 60 hours and the solvent evaporated to yield the titled product.

Intermediate C2

[2-(2-Fluoro-ethyl)-2H-tetrazol-5-yl]-ethylamine hydrochloride

Step 1: [2-(2H-Tetrazol-5-yl)-ethyl]-carbamic acid tert-butyl ester
This material was prepared by the protocols outlined in N. A. Delaney et al, European patent specification EP 449523.
Step 2: {2-[2-(2-Fluoro-ethyl)-2H-tetrazol-5-yl]-ethyl}-carbamic acid tert-butyl ester
To a solution of [2-(2H-Tetrazol-5-yl)-ethyl]-carbamic acid tert-butyl ester 0.45 g, 2.11 mmol) in dry DMF (14 ml) was suspended Cs2CO3 (0.825 g, 2.53 mmol) and the reaction mixture stirred for 15 minutes. 1-Bromo-2-fluoroethane (0.63 ml, 8.44 mmol) was added and the reaction mixture stirred at ambient temperature for 5 hours. The reaction mixture was filtered and the DMF evaporated to afford the crude product as a brown oil. The crude material was absorbed onto silica and purified by silica chromatography eluting with a gradient of 3:1 to 2:1 Ethylacetate:hexane to afford the titled product as a colorless oil.
Step 3: 2-[2-(2-Fluoro-ethyl)-2H-tetrazol-5-yl]-ethylamine hydrochloride A solution of {2-[2-(2-Fluoro-ethyl)-2H-tetrazol-5-yl]-ethyl}-carbamic acid tert-butyl ester (1.0 g, 3.9 mmol) in dichloromethane (30 ml) was treated with a solution of 4M HCl in dioxane (31 ml) and the reaction mixture stirred for 1 hour. The solvent was evaporated to yield the titled product as a white solid.

The following amine intermediates of formula (D)

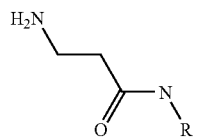

D are shown in the Table 4 below, the method of preparation being described hereinafter.

TABLE 4

| Intermediate | R |
|---|---|
| D1 | —CH2CH2F |
| D2 | —CH2CHF2 |
| D3 | —CH2CF3 |
| D4 | C(CH3)2CH2F |

Preparation
3-Amino-N-(2-fluoro-ethyl)-propionamide (D1)

Step 1: [2-(2-Fluoro-ethylcarbamoyl)-ethyl]-carbamic acid tert-butyl ester
3-tert-Butoxycarbonylamino-propionic acid (2.16 g, 11.4 mmol)) was dissolved in dichloromethane (80 ml) and cooled to 0° C. in an ice bath. [3-(Dimethylamino)propyl]ethylcarbodiimide hydrochloride (2.84 g, 14.8 mmol), hydroxybenzatriazole (1.54 g, 11.4 mmol) and triethylamine (7.9 ml, 57 mmol) were added and the reaction mixture stirred for 15 minutes. 2-fluoroethylamine hydrochloride (1.134 g, 11.4 mmol) was added in a single portion and then left to stir for 2 hours. The reaction mixture was partitioned between dichloromethane and water. The organic phase was dried over magnesium sulphate and evaporated. The crude product was purified by chromatography on silica using 2:3 iso-hexane: ethylacetate as eluant to afford the product.
Step 2: 3-Amino-N42-fluoro-ethyl)-propionamide A solution of [2-(2-Fluoro-ethylcarbamoyl)-ethyl]-carbamic acid tert-butyl ester (0.353 g, 1.51 mmol) in dichloromethane (10 ml) was treated with trifluoroacetic acid (1 ml) and the reaction stirred at ambient temperature for 4 hours. The solvent was evaporated to dryness to yield the titled product as a trifluoroacetate salt.

Amine intermediates (D) that are used to prepare the compounds of Examples 1 to 8 hereinafter are commercially available or are prepared by the procedure that is analogous to that described for D1.

Certain starting materials used to prepare amine intermediates (D) for preparation of compounds of the invention are not commercially available but are reported in the literature. E,g, 2-Fluoro-1,1-dimethyl-ethylamine is described in D. Ok, M. H. Fisher, M. J. Wyvratt and P. T. Meink, Tetrahedron Lett., 1999, 40 (20), 3831-3834. 222-Trifluoro-1,1-dimethyl-ethylamine is described in N. Zhang and S. Ayral-Kaloustian, J. Fluorine. Chem., 2002, 117, 9-11.

Preparation of Specific Examples:
General Procedure for Preparation of Urea Examples from Imidazole-Urea Intermediates (B) and Amines (C) or (D):

The amine (0.12 mmol) in dry DMF (0.12 mmol) is added to a solution/suspension of the imidazole urea intermediate (0.11 mmol) in DMF (1.0 ml). Triethylamine may be added to enhance reaction rate and especially if one or both of the starting materials is present as a salt (1.1 equivalents Et3N per equiv. salt). The reaction mixture may be sonicated if necessary until a clear solution was obtained. The reaction is allowed to proceed at between room temperature and 70° C. until the starting material is consumed (30 minutes to 24 hours). When complete, the mixture is concentrated in vacuo to remove the solvent. The product may be purified by dissolving the crude residue in THF (2 ml) and adding this to polymer supported isocyanate (Argonaut Technologies, 0.5 g, 1.10 mmol) which has been pre-swollen with THF (2 ml). The reaction mixture is allowed to drip through the resin under gravity and the solvent is removed in vacuo to yield the titled compound. Alternatively the product may be purified by standard procedure, e.g. crystallisation, chromatography or HPLC.

A typical example is as follows:

Example 8

1-{2-[2-(2-Fluoro-ethyl)-2H-tetrazol-5-yl]-ethyl}-3-[5-(3-fluoro-4-methanesulfonyl-phenyl)-4-methyl-thiazol-2-yl]-urea (NVP-QAV572)

Step 3: To a stirred solution of 2-[2-(2-Fluoro-ethyl)-2H-tetrazol-5-yl]-ethylamine hydrochloride (0.150 g, 0.0.77 mmol) in DMF (5 ml) was added triethylamine 0.243 ml, 0.1.74 mmol) followed by imidazole-1-carboxylic acid [5-(3-fluoro-4-methanesulfonyl-phenyl)-4-methyl-thiazol-2-yl]-amide (0.265 g, 0.7 mmol). After stirring at room temperature for 3.5 hours, the reaction mixture was filtered and water (3 ml) is added to the filtrate with vigorous stirring. The resulting solid was filtered and dried under high vacuum to yield the titled product as a white solid.

The compounds of Examples (1) to (7) are prepared analogously using the general procedure for preparation of urea examples from imidazole-urea intermediates (B) and amines (C) or (D) that is detailed above.

Compounds of formula I which are also of formula XVI

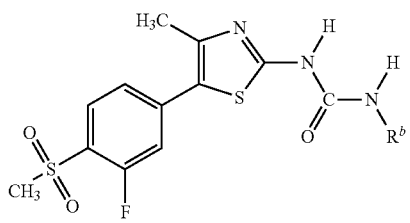

are shown in Table 8 below, the method of preparation being described hereinafter. The table also shows mass spectrometry data. The Examples are in free form.

TABLE 8

| Ex. | $R^b$ | M/s MH+ |
|---|---|---|
| 1 | | 457.2 |
| 2 | | 465.1 |
| 3 | | 447.1 |
| 4 | | 511.2 |
| 5 | | 483.2 |
| 6 | | 520.2 |

TABLE 8-continued

| Ex. | $R^b$ | M/s MH+ |
|---|---|---|
| 7 | | 470.3 |
| 8 | | 472.3 |

The invention claimed is:

1. A compound of formula Ia

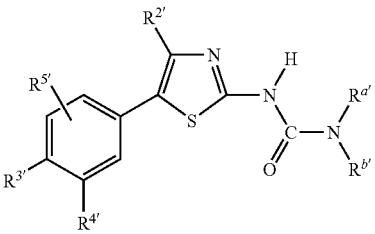

wherein: $R^{a*}$ is hydrogen or $C_1$-$C_4$-alkyl;
$R^{b*}$ is —($C_1$-$C_4$-alkylene)-Y—$C_1$-$C_4$-fluoroalkyl;
Y represents —CONH— or a five membered heteroaryl group
$R^{2*}$ is $C_1$-$C_4$-alkyl or halogen;
$R^{3*}$ is halo, —$SO_2$—$CH_3$, —$SO_2$—$CF_3$, —CO—$NH_2$, —CO-di($C_1$-$C_8$-alkyl)amino, or a 5- or 6-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino;
$R^{4*}$ is hydrogen, halo, —$SO_2$—$CH_3$, nitrile, $C_1$-$C_8$-haloalkyl, imidazolyl, $C_1$-$C_8$-alkyl, —$NR^{8*}R^{9*}$, or —$SO_2$—$NR^{8*}R^{9*}$; and
$R^{5*}$ is hydrogen, halogen or $C_1$-$C_8$-alkyl;
$R^{8*}$ and $R^{9*}$ are independently hydrogen, amino, $C_1$-$C_8$-alkylamino, di($C_1$-$C_8$-alkyl)amino, or $C_1$-$C_8$-alkyl optionally substituted by hydroxyl; or a pharmaceutically acceptable salt thereof.

2. A compound according to claim 1 where $R^{a*}$ is H.

3. A compound according to claim 1 where $R^{b*}$ is —($C_1$-$C_4$-alkylene)-Y-$C_1$-$C_4$-fluoroalkyl, where Y represents a —CONH— or a five membered heteroaryl group, $C_1$-$C_4$-alkylene represents ethylene and $C_1$-$C_4$-fluoroalkyl represents 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl.

4. A compound according to claim 3 where Y is CONH or a five membered heteroaryl group selected from imidazolyl or tetrazolyl.

5. A compound according to any one of claims 1-4 where $R^{2*}$ is $C_1$-$C_4$-alkyl.

6. A compound according to any one of claims 1-4 where $R^{3*}$ is —$SO_2$—$CH_3$.

7. A compound according to any one of claims 1-4 where $R^{4*}$ is fluoro.

8. A compound according to any one of claims 1-4 where $R^{5*}$ is hydrogen.

9. A compound according to claim 1, represented by a compound of formula (Ib)

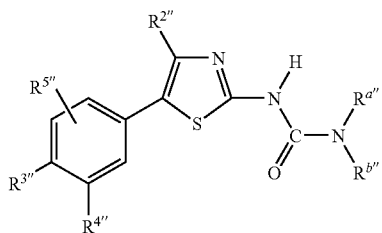

wherein
$R^{a**}$ is H;
$R^{b**}$ is —($C_1$-$C_4$-alkylene)-Y—$C_1$-$C_4$-fluoroalkyl;
Y represents a —CONH— or a five membered heteroaryl group;
$R^{2**}$ is $C_1$-$C_4$-alkyl;
$R^{3**}$ is —$SO_2$—$CH_3$;
$R^{4**}$ is fluoro; and
$R^{5**}$ is hydrogen, or a pharmaceutically acceptable salt, thereof.

10. A compound according to claim 2 where $R^{b*}$ is —($C_1$-$C_4$-alkylene)-Y—$C_1$-$C_4$-fluoroalkyl, where Y represents a —CONH— or a five membered heteroaryl group, $C_1$-$C_4$-alkylene represents ethylene and $C_1$-$C_4$-fluoroalkyl represents 1,1-dimethyl-2-fluoroethyl, 2,2-difluoroethyl, 2-fluoroethyl, 1,1-dimethyl-2,2,2-trifluoroethyl, 2,2,2-trifluoroethyl or 3,3,3-trifluoropropyl.

11. A compound according to claim 10 where Y is CONH or a five membered heteroaryl group selected from imidazolyl or tetrazolyl.

12. A compound according to any one of claims 10-11 where $R^{2*}$ is $C_1$-$C_4$-alkyl.

13. A compound according to any one of claims 10-11 where $R^{3*}$ is —$SO_2$—$CH_3$.

14. A compound according to any one of claims 10-11 where $R^{4*}$ is fluoro.

15. A compound according to any one of claims 10-11 where $R^{5*}$ is hydrogen.

* * * * *